(12) United States Patent
Lin et al.

(10) Patent No.: US 11,844,882 B2
(45) Date of Patent: Dec. 19, 2023

(54) VEHICLE-MOUNTED INTELLIGENT FRAGRANCE GENERATOR

(71) Applicant: XIAMEN MAXMAC AIR TECHNOLOGY CO., LTD., Xiamen (CN)

(72) Inventors: Yangxin Lin, Xiamen (CN); Depei Wu, Xiamen (CN); Jianbo Wang, Xiamen (CN); Changping Lin, Xiamen (CN); Hongzhe Peng, Xiamen (CN)

(73) Assignee: XIAMEN MAXMAC AIR TECHNOLOGY CO., LTD., Xiamen (CN)

( * ) Notice: Subject to any disclaimer, the term of this patent is extended or adjusted under 35 U.S.C. 154(b) by 158 days.

(21) Appl. No.: 17/456,379

(22) Filed: Nov. 24, 2021

(65) Prior Publication Data

US 2023/0098152 A1    Mar. 30, 2023

(30) Foreign Application Priority Data

Sep. 17, 2021    (CN) .......................... 202122264841.1

(51) Int. Cl.
*A61L 9/12* (2006.01)
*B60H 3/00* (2006.01)

(52) U.S. Cl.
CPC ............ *A61L 9/122* (2013.01); *B60H 3/0092* (2013.01); *A61L 2209/133* (2013.01); *A61L 2209/15* (2013.01)

(58) Field of Classification Search
None
See application file for complete search history.

(56) References Cited

U.S. PATENT DOCUMENTS

2019/0263527 A1* 8/2019 Fantuzzi ................. B01F 25/00

* cited by examiner

*Primary Examiner* — Jelitza M Perez
(74) *Attorney, Agent, or Firm* — Bayramoglu Law Offices LLC

(57) ABSTRACT

A vehicle-mounted intelligent fragrance generator includes a casing and a plurality of essence boxes. The casing includes a base. Each essence box includes an outer sleeve, an inner sleeve, an essence block and a fragrance front cover, the outer sleeve has a protrusion, and the protrusion is disposed at a front end portion of an inner wall of the outer sleeve. A rear end of the inner sleeve is a closed end, a front end is an open end, and the front end of an outer wall of the inner sleeve is provided with an anti-rotation strip. The outer sleeve is fixed inside the base, the outer sleeve, the inner sleeve and the essence block are sequentially sleeved, the front end of the inner sleeve protrudes from the outer sleeve and extends out of the base, and the anti-rotation strip is clamped on the protrusion of the outer sleeve.

9 Claims, 11 Drawing Sheets

VEHICLE-MOUNTED INTELLIGENT FRAGRANCE GENERATOR

CROSS REFERENCE TO THE RELATED APPLICATIONS

This application is based upon and claims priority to Chinese Patent Application No. 202122264841.1, filed on Sep. 17, 2021, the entire contents of which are incorporated herein by reference.

TECHNICAL FIELD

The present invention relates to the field of fragrance devices, in particular to a vehicle-mounted intelligent fragrance generator.

BACKGROUND

A fragrance device can release different fragrance scents into the air by the aid of an essence source, improve the exterior space environment, and create a comfortable atmosphere for users. At present, the fragrance device is often mounted in a car or indoors to improve the in-car environment or indoor environment. The fragrance device generally includes a draft fan, a motor, a shunt shaft sleeve, a shunt rotor, an essence box and the like. Since there are a great variety of components, the current fragrance device generally includes a fixing bracket for mounting the components such as the shunt shaft sleeve, the shunt rotor and the essence box. As a result, the volume of the fragrance device is too large. When the fragrance device is mounted in the car, it is hard to place and takes up too much space since there is only a small space for placement in the car.

SUMMARY

In order to solve the above technical problems, the present invention provides a vehicle-mounted fragrance generator whose lateral dimension can be greatly reduced.

The technical solution of the present invention is as follows: provided is a vehicle-mounted intelligent fragrance generator, including a casing and a plurality of essence boxes. The casing includes a base. Each of the essence boxes includes an outer sleeve, an inner sleeve, an essence block and a fragrance front cover, the outer sleeve has a protrusion, and the protrusion is disposed at a front end portion of an inner wall of the outer sleeve. A rear end of the inner sleeve is a closed end, a front end is an open end, and the front end of an outer wall of the inner sleeve is provided with an anti-rotation strip. The outer sleeve is fixed inside the base, the outer sleeve, the inner sleeve and the essence block are sequentially sleeved, the front end of the inner sleeve protrudes from the outer sleeve and extends out of the base, and the anti-rotation strip is clamped on the protrusion of the outer sleeve. The fragrance front cover is located outside the base and fastened to a front end portion of the inner sleeve.

The structure of the essence boxes is brand-new. The essence boxes of this structure can be directly placed inside the base of the casing, and the fragrance switching assembly can be directly placed on the essence boxes. Therefore, the volume of the fragrance generator is effectively reduced, and the space taken up by the fragrance generator is reduced.

Preferably, a force applied on the anti-rotation strip by the protrusion of the outer sleeve is F1. One side of the base is provided with a plurality of through holes, a convex ring is disposed in each of the through holes, and the convex ring is broken to form at least one notch and at least one arc strip. The front end of the outer wall of the inner sleeve is further provided with at least one L-shaped protruding strip, and the L-shaped protruding strip is located at the front of the anti-rotation strip. The front end of the inner sleeve extends out of the through hole of the base, a vertical edge of the L-shaped protruding strip is located in the notch, the L-shaped protruding strip is stopped by the arc strip, a circumferential force applied on the L-shaped protruding strip by the arc strip is F2, and F2 and F1 are opposite in direction. The inner sleeve receives the forces F2 and F1 in two opposite directions along the circumferential direction, and can be well fixed in the outer sleeve and the base.

Preferably, the outer sleeves are disposed in parallel and integrally formed, and a connecting rib is integrally formed between every two adjacent outer sleeves.

Preferably, the vehicle-mounted intelligent fragrance generator further includes a main control printed circuit board assembly (PCBA) board and an identification circuit board for identifying the type of fragrance. The main control PCBA board and the identification circuit board are in communication connection. The identification circuit board is provided with a plurality of pin connector groups. An identity (ID) identification chip is embedded in a rear end portion of each of the inner sleeves, and each of the pin connector groups is respectively connected to the corresponding one ID identification chip.

Preferably, the vehicle-mounted intelligent fragrance generator further includes a draft fan and a fragrance switching assembly. The casing further includes a first air inlet 14 and a first air outlet. The outer sleeve further has an air inlet pipe port and an air outlet pipe port, and the outer wall of the inner sleeve has a plurality of fragrance diffusion holes. The air inlet pipe port communicates with one fragrance diffusion hole, and the air outlet pipe port communicates with another fragrance diffusion hole. The air inlet pipe port and the air outlet pipe port of one of the outer sleeves respectively communicate with an intake opening and a discharge opening of the draft fan through the fragrance switching assembly. The intake opening of the draft fan communicates with the first air inlet 14, and the discharge opening of the draft fan communicates with the first air outlet.

Preferably, the casing further includes an upper casing, and the upper casing is buckled on the base to form a containing cavity. The first air inlet 14 and the first air outlet are disposed in the upper casing. The draft fan and the fragrance switching assembly are both located in the containing cavity, and the draft fan, the fragrance switching assembly and the outer sleeve are sequentially disposed from top to bottom. The draft fan, the fragrance switching assembly and the outer sleeve are sequentially disposed from top to bottom, thereby effectively saving the lateral space and greatly reducing the volume of the fragrance generator.

Preferably, the fragrance switching assembly includes a shunt shaft sleeve, a shunt rotor and a motor. The shunt shaft sleeve is provided with a first air inlet pipe connector, a second air outlet and three sets of air pipes, the first air inlet pipe connector communicates with the first air inlet through the draft fan, and the second air outlet communicates with the first air outlet through the draft fan. Each set of air pipes includes an air inlet pipe and an air outlet pipe, the air inlet pipe communicates with the air inlet pipe port of one of the outer sleeves, and the air outlet pipe communicates with the air outlet pipe port of the outer sleeve. The shunt rotor includes a plurality of third air inlets, a lead-in port and a lead-out port. The plurality of third air inlets are distributed along a circumferential direction of the shunt rotor, and the lead-in port, the lead-out port and one of the third air inlets are distributed along an axial direction of the shunt rotor. The shunt rotor is rotatably disposed inside the shunt shaft sleeve. The first air inlet pipe connector communicates with one of the third air inlets and forms a clearance seal fit with the third air inlet. The air inlet pipe communicates with the lead-in port through a first channel inside the shunt rotor, and the lead-out port communicates with the second air outlet through a second channel inside the shunt rotor. The motor drives the shunt rotor to rotate in the shunt shaft sleeve.

Preferably, the vehicle-mounted intelligent fragrance generator further includes a travel switch. The travel switch includes a motor, a control dial, a photoelectric switch and a main control PCBA board 4. The motor drives the shunt rotor to rotate, the control dial is mounted on the shunt rotor, and the motor and the photoelectric switch are both electrically connected to the main control PCBA board 4. The control dial forms a clearance fit in the photoelectric switch, the control dial is provided with a plurality of sets of signal modules, each set of signal modules includes a locating module and a judgment module, the locating module is disposed next to the judgment module, and the judgment modules in the sets of signal modules are different.

Preferably, the judgment module includes at least one short hole, and the number of the short holes in each judgment module is different. The locating module includes one long hole. A depth of the short hole is less than a depth of the long hole.

The present invention has the following advantages: the essence boxes can be directly placed inside the base of the casing, the fragrance switching assembly can be directly placed on the essence boxes, and the essence boxes and the fragrance switching assembly can be fixed without an additional fixing bracket, thereby saving the parts and simplifying the structure. Therefore, the volume of the fragrance generator is effectively reduced, and the space taken up by the fragrance generator is reduced.

DETAILED DESCRIPTION OF THE EMBODIMENTS

Figure 1:
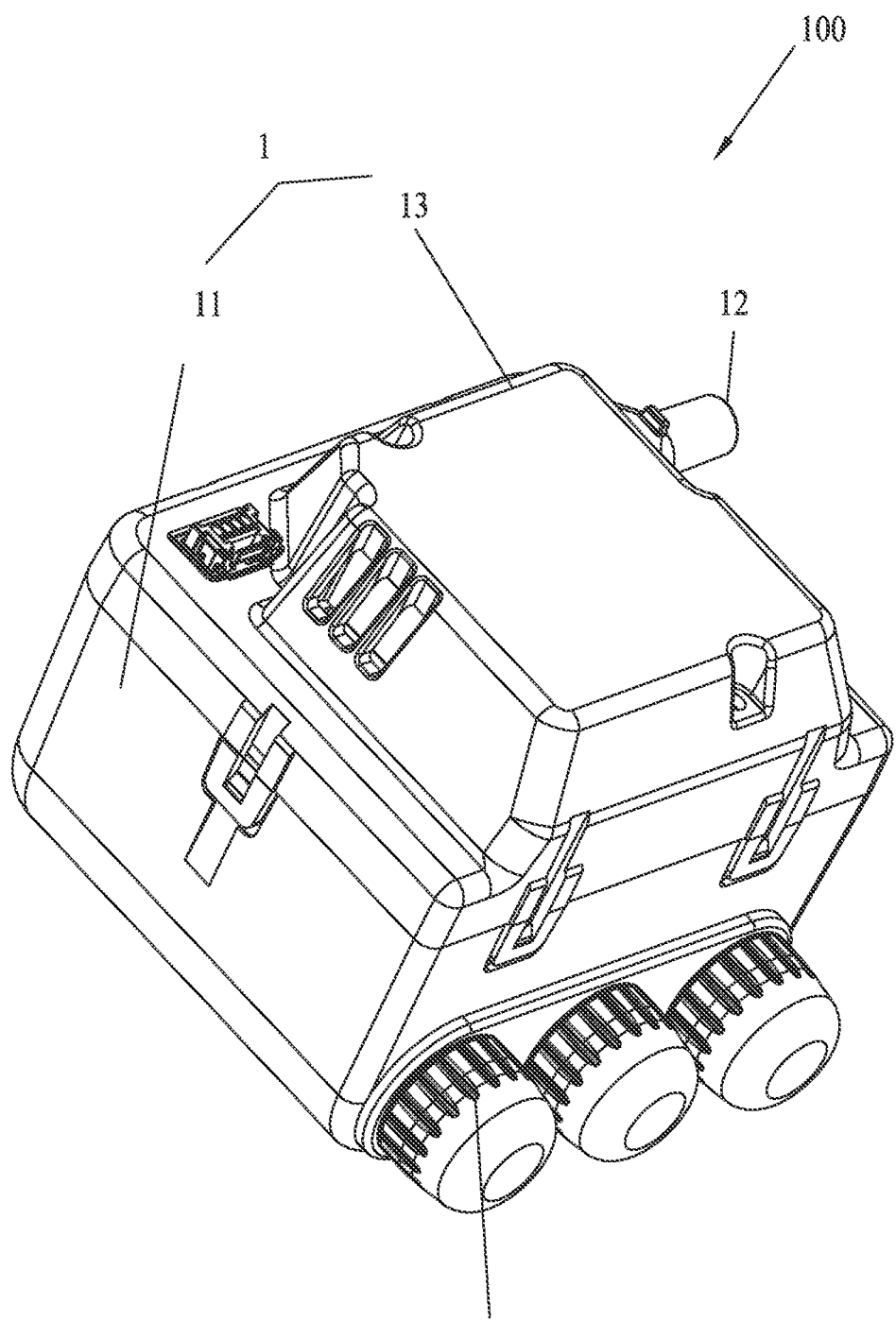
FIG. 1 is a front three-dimensional view of a vehicle-mounted intelligent fragrance generator of the present invention.
Figure 2:
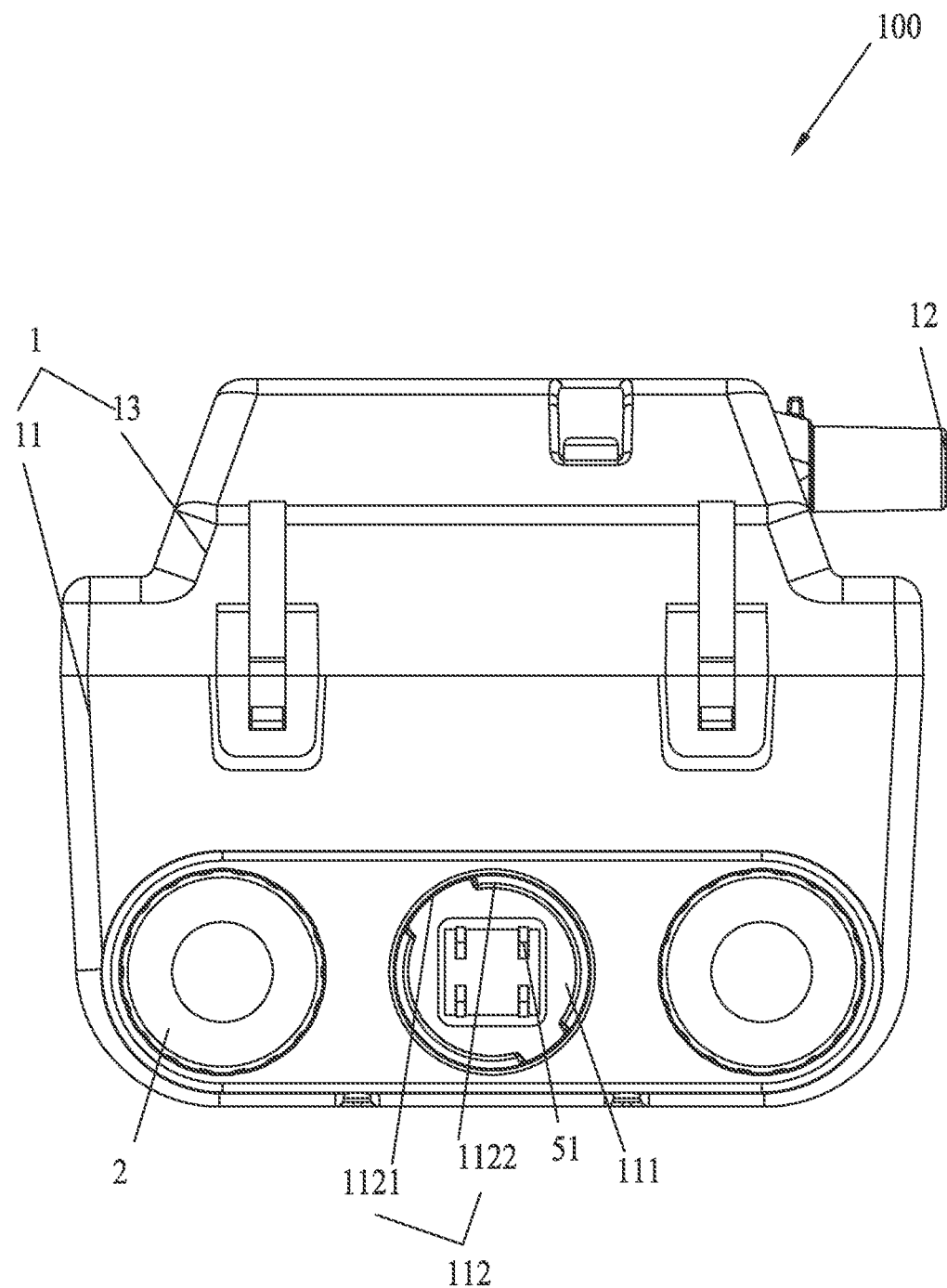
FIG. 2 is a side view of the vehicle-mounted intelligent fragrance generator of the present invention.

Embodiments of the present invention will be described in detail below. Examples of the embodiments are shown in the accompanying drawings. The same or similar reference numerals indicate the same or similar elements or elements with the same or similar functions. The embodiments described with reference to the accompanying drawings below are exemplary, and are intended to explain the present invention, but should not be construed as limiting the present invention.

A front end portion of an inner sleeve 22 refers to the end portion at an open end 223 of the inner sleeve 22, and a rear end portion of the inner sleeve 22 refers to the end portion at a closed end 222 of the inner sleeve 22. The direction of the front and rear ends of the outer sleeve 21 is the same as the direction of the front and rear ends of the inner sleeve 22.

Referring to FIGS. 1-4, a vehicle-mounted intelligent fragrance generator 100 includes a casing 1, a draft fan 6, a fragrance switching assembly 7, a plurality of essence boxes 2, a main control PCBA board 4, an identification circuit board 5 for identifying the type of fragrance, and a travel switch K. The casing 1 includes an upper casing 13, a base 11, a first air inlet 14 and a first air outlet 12. The upper casing 13 is buckled on the base 11 to form a containing cavity j. The first air inlet 14 and the first air outlet 12 are disposed in the upper casing 13.

Figure 3:
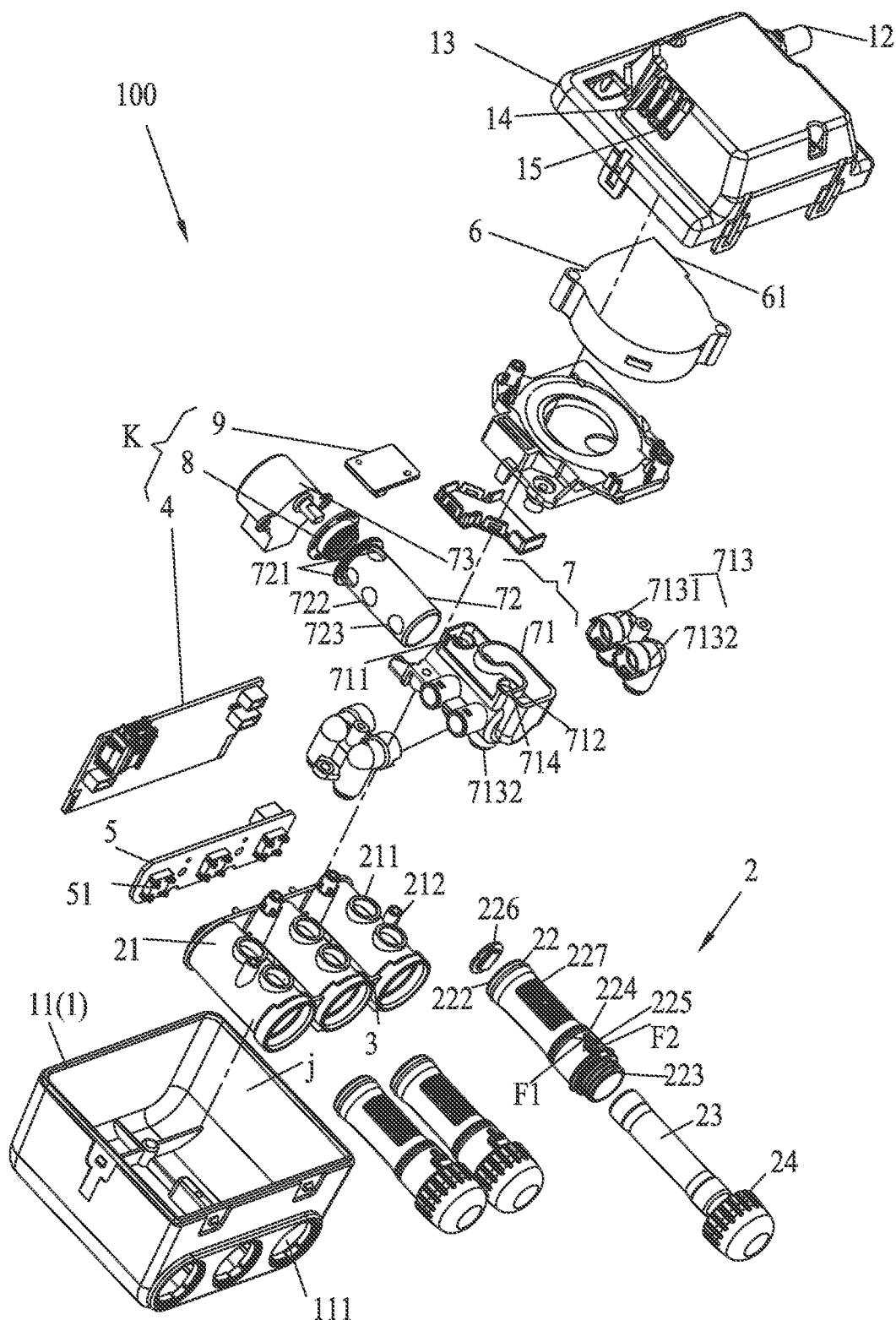
FIG. 3 is an exploded view of the vehicle-mounted intelligent fragrance generator of the present invention.

Referring to FIG. 3, in this embodiment, there are 3 essence boxes 2. The essence boxes 2 respectively have different fragrance scents. Each of the essence boxes 2 includes an outer sleeve 21, an inner sleeve 22, an essence block 23 and a fragrance front cover 24. The outer sleeves 21 are disposed in parallel and integrally formed, and a connecting rib 3 is integrally formed between every two adjacent outer sleeves 21. The outer sleeves 21 are connected into an integral structure through the connecting ribs 3 to become a whole, which is more convenient for assembly and can be directly and stably fixed in the base 11 without scattering. Thus, the fragrance switching assembly 7 can be directly placed on the outer sleeves 21, and the essence boxes 2 and the fragrance switching assembly 7 can be fixed together without using a fixing bracket, thereby saving the component fixing bracket, and greatly reducing the volume of the fragrance generator 100. Therefore, the components of the fragrance generator 100 can be well placed in a small space.

Referring to FIG. 1, FIG. 3 and FIGS. 5-6, the outer sleeve 21 has an air inlet pipe port 211, an air outlet pipe port 212 and a protrusion 213, and the protrusion 213 is disposed at a front end portion of an inner wall of the outer sleeve 21. A rear end of the inner sleeve 22 is a closed end 222, a front end is an open end 223, an outer wall of the inner sleeve 22 has a plurality of fragrance diffusion holes 227, and the front end of an outer wall of the inner sleeve 22 is provided with an anti-rotation strip 224. The front end of the outer wall of the inner sleeve 22 is further provided with at least one L-shaped protruding strip 225, and the L-shaped protruding strip 225 is located at the front of the anti-rotation strip 224. The outer sleeve 21 is fixed inside the base 11, the outer sleeve 21, the inner sleeve 22 and the essence block 23 are sequentially sleeved, the front end of the inner sleeve 22 protrudes from the outer sleeve 21 and extends out of the base 11, and the anti-rotation strip 224 is clamped on the protrusion 213 of the outer sleeve 21. A force applied on the anti-rotation strip 224 by the protrusion 213 of the outer sleeve 21 is F1. The disposition of the outer sleeve 21 and the inner sleeve 22 can prevent the essence blocks with different fragrance scents from tainting each other. The fragrance front cover 24 is located outside the base 11 and fastened to a front end portion of the inner sleeve 22. The fragrance front cover 24 and the inner sleeve 22 are connected detachably or non-detachably. When the essence block 23 needs to be replaced, the fragrance front cover 24 and the inner sleeve 22 can be connected detachably, and the fragrance front cover 24 serves as a holding part. When the essence block 23 needs to be replaced, the fragrance front cover 24 can be held to pull out the inner sleeve 22 and the essence block 23 together, and then the essence block 23 is replaced. Thus, the essence block in any one of the essence boxes 2 can be replaced independently without disassembling the casing 1. The air inlet pipe port 211 communicates with one fragrance diffusion hole 227, and the air outlet pipe port 212 communicates with another fragrance diffusion hole 227. The air inlet pipe port 211 and the air outlet pipe port 212 of one of the outer sleeves 21 respectively communicate with the first air inlet 14 and the first air outlet 12 in one-to-one correspondence sequentially through the fragrance switching assembly 7 and the draft fan 6. That is, the air inlet pipe port 211 and the air outlet pipe port 212 of one of the outer sleeves 21 respectively communicate with an intake opening and a discharge opening 61 of the draft fan 6 through the fragrance switching assembly 7. The intake opening of the draft fan 6 communicates with the first air inlet 14, and the discharge opening 61 of the draft fan 6 communicates with the first air outlet 12.

Referring to FIGS. 1-2 and FIGS. 5-6, one side of the base 11 is provided with a plurality of through holes 111, a convex ring 112 is disposed in each of the through holes 111, and the convex ring 112 is broken to form at least one notch 1121 and at least one arc strip 1122. The front end of the inner sleeve 22 extends out of the through hole 111 of the base 11, a vertical edge of the L-shaped protruding strip 225 is located in the notch 1121, the L-shaped protruding strip 225 is stopped by the arc strip 1122, a circumferential force applied on the L-shaped protruding strip 225 by the arc strip 1122 is F2, and F2 and F1 are opposite in direction. The arc strip 1122 clamps the vertical edge of the L-shaped protruding strip 225, which can prevent the inner sleeve 22 from rotation and locate the inner sleeve 22 in the circumferential direction. A lateral edge of the L-shaped protruding strip 225 is clamped by an inner bottom surface of the arc strip 1122, which can prevent the inner sleeve 22 from coming off the through hole 111 of the base 11 along the axial direction and locate the inner sleeve 22 in the axial direction. The forces F2 and F1 are opposite in direction, and the inner sleeve 22 receives the forces F2 and F1 in two opposite directions along the circumferential direction, and so the inner sleeve 22 can be well fixed in the outer sleeve 21 and the base 11. A width of the notch 1121 is equal to or greater than a length of the lateral edge of the L-shaped protruding strip 225, so when a component such as the inner sleeve 22 is inserted into the base 11, the notch 1121 can give way to the L-shaped protruding strip 225 of the inner sleeve 22.

Referring to FIGS. 3-4 and FIGS. 6-7, the fragrance switching assembly 7 includes a shunt shaft sleeve 71, a shunt rotor 72 and a motor 73. The shunt shaft sleeve 71 is provided with a first air inlet pipe connector 711, a second air outlet 712 and three sets of air pipes 713, the first air inlet pipe connector 711 communicates with the first air inlet 14 through the draft fan 6, and the second air outlet 712 communicates with the first air outlet 12 through the draft fan 6 (the discharge opening 61 of the draft fan 6). Each set of air pipes 713 includes an air inlet pipe 7131 and an air outlet pipe 7132, the air inlet pipe 7131 communicates with the air inlet pipe port 211 of one of the outer sleeves 21, and the air outlet pipe 7132 communicates with the air outlet pipe port 212 of the outer sleeve 21. The shunt rotor 72 includes a plurality of third air inlets 721, a lead-in port 722 and a lead-out port 723. The plurality of third air inlets 721 are distributed along a circumferential direction of the shunt rotor 72, and the lead-in port 722, the lead-out port 723 and one of the third air inlets 721 are distributed along an axial direction of the shunt rotor 72. The shunt rotor 72 is rotatably disposed inside the shunt shaft sleeve 71. The motor 73 drives the shunt rotor 72 to rotate in the shunt shaft sleeve 71. The first air inlet pipe connector 711 communicates with one of the third air inlets 721 and forms a clearance seal fit with the third air inlet 721. The air inlet pipe 7131 communicates with the lead-in port 722 through a first channel a inside the shunt rotor 72, and the lead-out port 723 communicates with the second air outlet 712 through a second channel b inside the shunt rotor 72. The draft fan 6 and the fragrance switching assembly 7 are both located in the containing cavity j, and the draft fan 6, the fragrance switching assembly 7 and the outer sleeve 21 are sequentially disposed from top to bottom. The draft fan 6, the fragrance switching assembly 7 and the outer sleeve 21 are sequentially disposed from top to bottom, thereby effectively saving the lateral space and greatly reducing the volume of the fragrance generator 100. The essence boxes 2 have different fragrance scents. Air flows through the first air inlet 14, the intake opening of the draft fan 6, the first air inlet pipe connector 711 of the shunt shaft sleeve 71, one of the third air inlets 721 of the shunt rotor 72, the first channel a inside the shunt rotor 72, the air inlet pipe 7131 of the shunt shaft sleeve 71 and the air inlet pipe port 211 of one of the outer sleeves 21, and is mixed with the essence in the essence box 2 to form fragrance gas. Then, the fragrance gas flows through the air outlet pipe port 212 of the outer sleeve 21, the air outlet pipe 7132, the lead-out port 723 of the shunt rotor 72, the second channel b inside the shunt rotor 72, the second air outlet 712, the air outlet pipe port 212 and the first air outlet 12, and is finally released to the exterior space environment to improve the space environment of the user. To switch among the fragrance scents, the user only needs to rotate the shunt rotor 72 to make the lead-in port 722 and the lead-out port 723 of the shunt rotor 72 respectively connected to another set of air inlet pipe 7131 and air outlet pipe 7132, so that the air can communicate with the corresponding essence box 2. Switching among different fragrance scents can satisfy preferences of different users.

Figure 10:
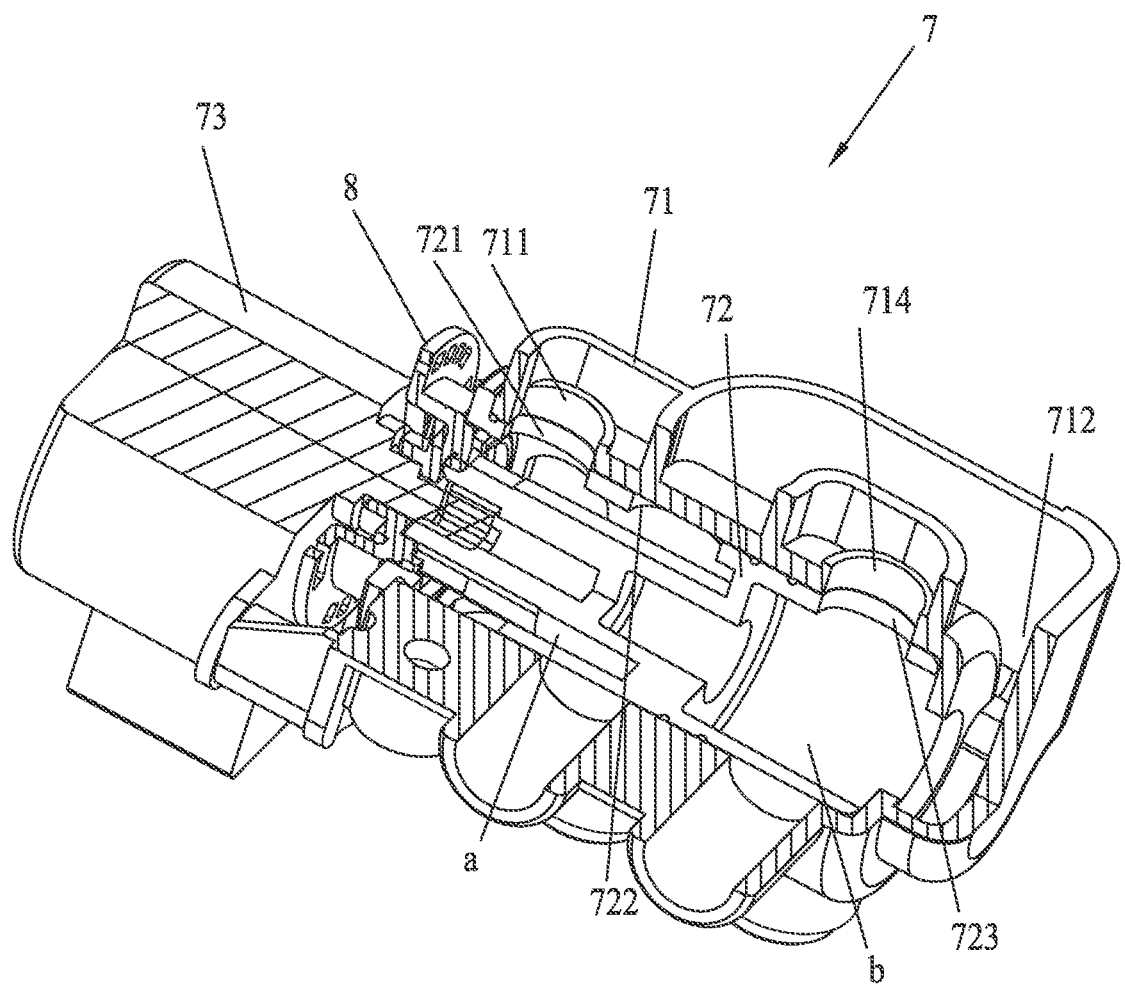
FIG. 10 is a schematic diagram of the fragrance switching assembly in an operating state IV in the present invention.

Referring to FIG. 3 and FIG. 10, the upper casing 13 is further provided with a second air inlet 15, and the shunt shaft sleeve 71 is further provided with a second air inlet pipe connector 714. The second air inlet pipe connector 714 communicates with the second air inlet 15, and the second air inlet pipe connector 714 forms a clearance seal fit with the lead-out port 723 in the shunt rotor 72. During operation, the user can also rotate the shunt rotor 72 to make the lead-out port 723 in the shunt rotor 72 communicate with the second air inlet pipe connector 714. At this time, even if the first air inlet 14 communicates with the third air inlet 721 through the first air inlet pipe connector 711, there is no air flow in the first channel a in the shunt rotor 72 since the lead-in port 722 is in a closed state. Under the action of the draft fan 6, the air sequentially flows through the second air inlet 15 (not shown), the second air inlet pipe connector 714, the lead-out port 723, the second channel b in the rotor, the second air outlet 712, the draft fan 6 and the first air outlet 12, and is blown to the exterior space environment to form natural wind with no fragrance scent, thereby increasing the use functions of the fragrance generator.

Figure 11:
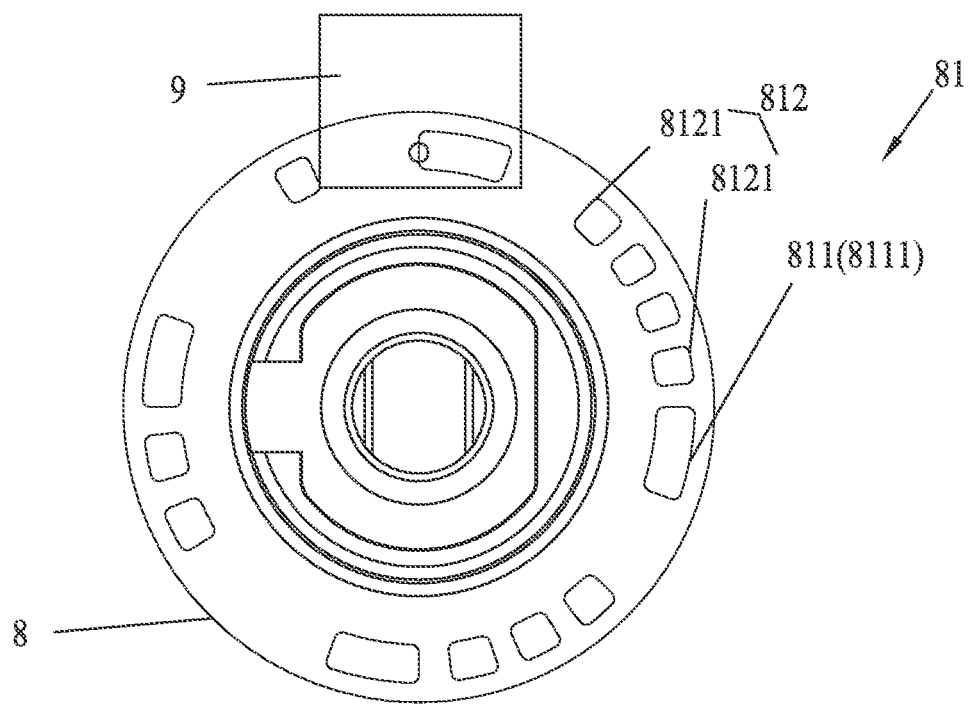
FIG. 11 is a schematic diagram I of a control dial and a photoelectric switch in fit in the present invention.
Figure 12:
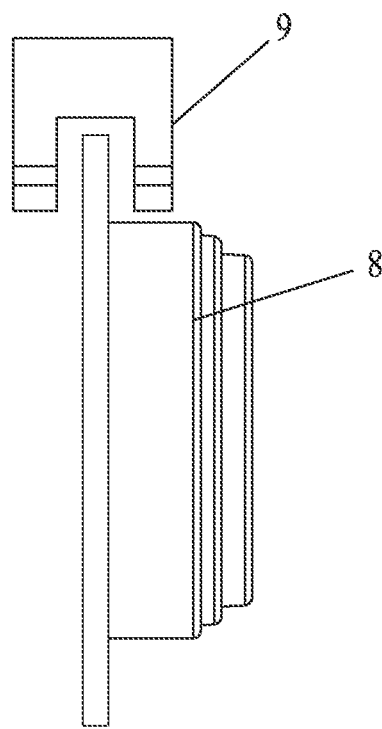
FIG. 12 is a schematic diagram II of the control dial and the photoelectric switch in fit in the present invention.

Referring to FIG. 3 and FIGS. 11-12, the travel switch K includes a motor 73, a control dial 8, a photoelectric switch 9 and a main control PCBA board 4. The motor 73 drives the shunt rotor 72 to rotate, the control dial 8 is mounted on the shunt rotor 72, and the motor 73 and the photoelectric switch 9 are both electrically connected to the main control PCBA board 4. The control dial 8 forms a clearance fit in the photoelectric switch 9, the control dial 8 is provided with a plurality of sets of signal modules 81, each set of signal modules 81 includes a locating module 811 and a judgment module 812, the locating module 811 is disposed next to the judgment module 812, and the judgment modules 812 in the sets of signal modules 81 are different. The judgment module 812 includes at least one short hole 8121, and the number of the short holes 8121 in each judgment module 812 is different. The locating module 811 includes one long hole 8111. A depth of the short hole 8121 is less than a depth of the long hole 8111. In this embodiment, the control dial 8 is provided with four different sets of signal modules 81. The four different sets of signal modules 81 respectively correspond to four operating states of the fragrance switching assembly 7, three of which are the operating states in which the air respectively communicates with the three essence boxes 2 and the other is the operating state in which the air communicates with the second air inlet 15.

Referring to FIG. 3 and FIGS. 10-11, during the operation, the main control PCBA board 4 can distinguish different operating states of the fragrance switching assembly 7 through the judgment module 812 and control the fragrance switching assembly 7 to execute the corresponding operating state through the locating module 811. For example, when the user needs the fragrance switching assembly 7 to execute the operating state in which the air communicates with the second air inlet 15, the main control PCBA board 4 firstly controls the motor 73 to operate, the motor 73 drives the shunt rotor 72 to rotate on the shunt shaft sleeve, and the control dial 8 mounted on the shunt rotor 72 rotates along with the shunt rotor 72 and rotates in the photoelectric switch 9. The signal modules 81 on the control dial 8 sequentially pass through the photoelectric switch 9 as the control dial rotates. After the judgment module 812 in the signal module 81 corresponding to the above operating state passes through the photoelectric switch 9, the main control PCBA board 4 makes an identification and a determination, then the locating module 811 in the signal module 81 passes through the photoelectric switch 9, the main control PCBA board 4 makes an identification and a determination, and controls the motor 73 to give a response and perform execution, that is, to stop rotation, so that the shunt rotor 72 stops at the operating state in which the air communicates with the second air inlet 15.

Referring to FIG. 3 and FIGS. 11-12, the judgment module 812 includes at least one short hole 8121, and the number of the short holes 8121 in each judgment module 812 is different. The locating module 811 includes one long hole 8111. A depth of the short hole 8121 is less than a depth of the long hole 8111. In this embodiment, the four sets of signal modules 81 on the control dial 8 are: the first signal module 81 including 1 short hole 8121 and 1 long hole 8111, the second signal module 81 including 2 short holes 8121 and 1 long hole 8111, the third signal module 81 including 3 short holes 8121 and 1 long hole 8111, and the fourth signal module 81 including 4 short holes 8121 and 1 long hole 8111. The four different sets of signal modules 81 respectively correspond to four operating states of the fragrance switching assembly 7. During the rotation of the control dial 8, the photoelectric switch 9 scans the short hole 8121 and the long hole 8111 in the control dial 8, thereby generating high and low voltage signals with different time lengths. When the short hole 8121 passes through the photoelectric switch 9, a short-time signal is generated. When the long hole 8111 passes through the photoelectric switch 9, a long-time signal is generated. The main control PCBA board 4 controls the motor 73 according to the short-time signals and the long-time signal collected by the photoelectric switch 9. Different numbers of the short-time signals are used as a judgment signal, and the long-time signal is used as an execution signal. In the present invention, the travel switch K configured to control the rotation of the shunt rotor 72 is disposed. Through the fit between the photoelectric switch 9 and the control dial 8, the travel switch K provides the main control PCBA board 4 with a basis for identifying and controlling the operating state of the fragrance switching assembly 7. On such a basis, the main control PCBA board 4 controls the motor 73 and further controls the shunt rotor 72, thereby realizing intellectual operation on the control of the rotation of the shunt rotor 72.

Figure 4:
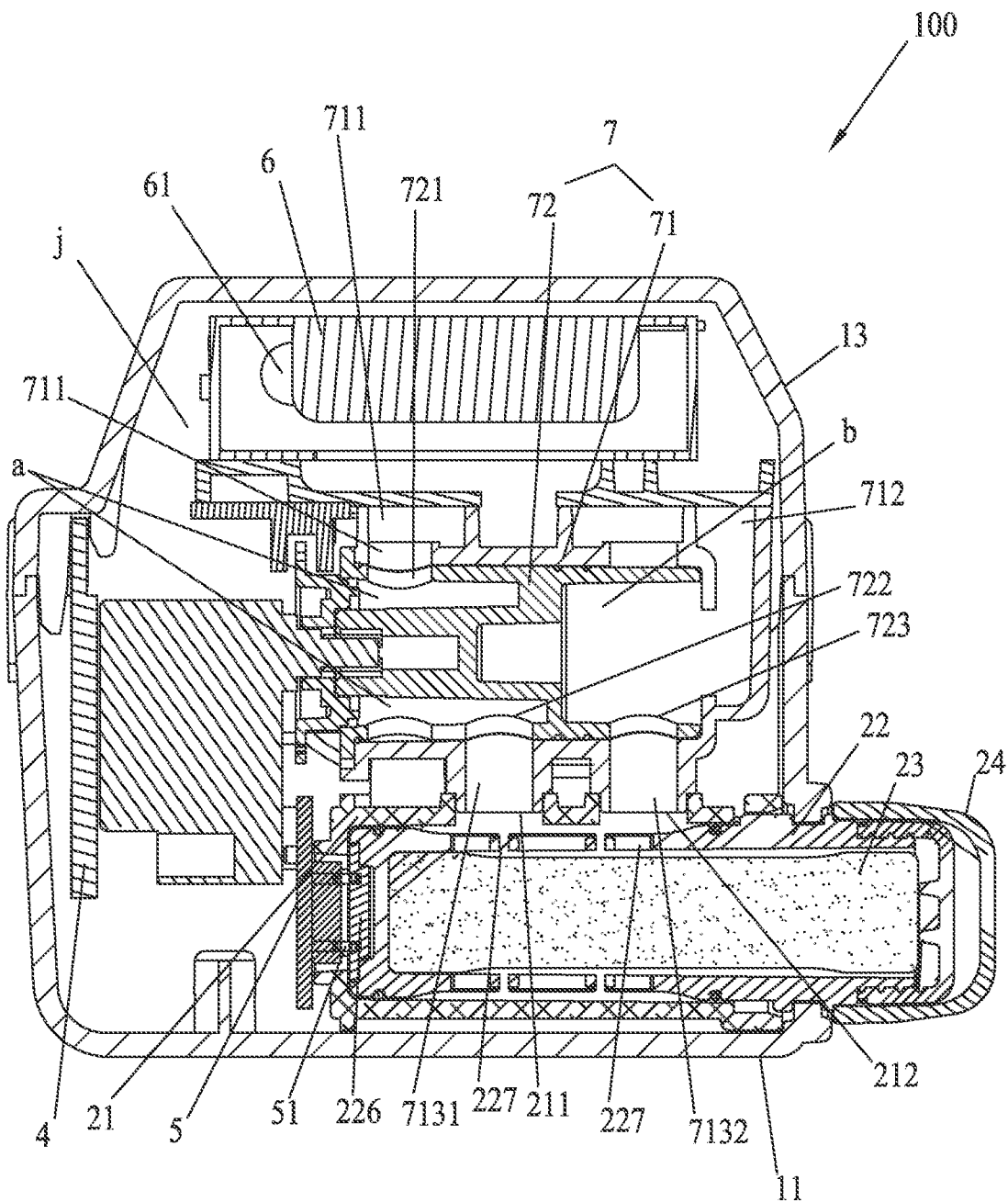
FIG. 4 is a cross-sectional view of the vehicle-mounted intelligent fragrance generator of the present invention.
Figure 5:
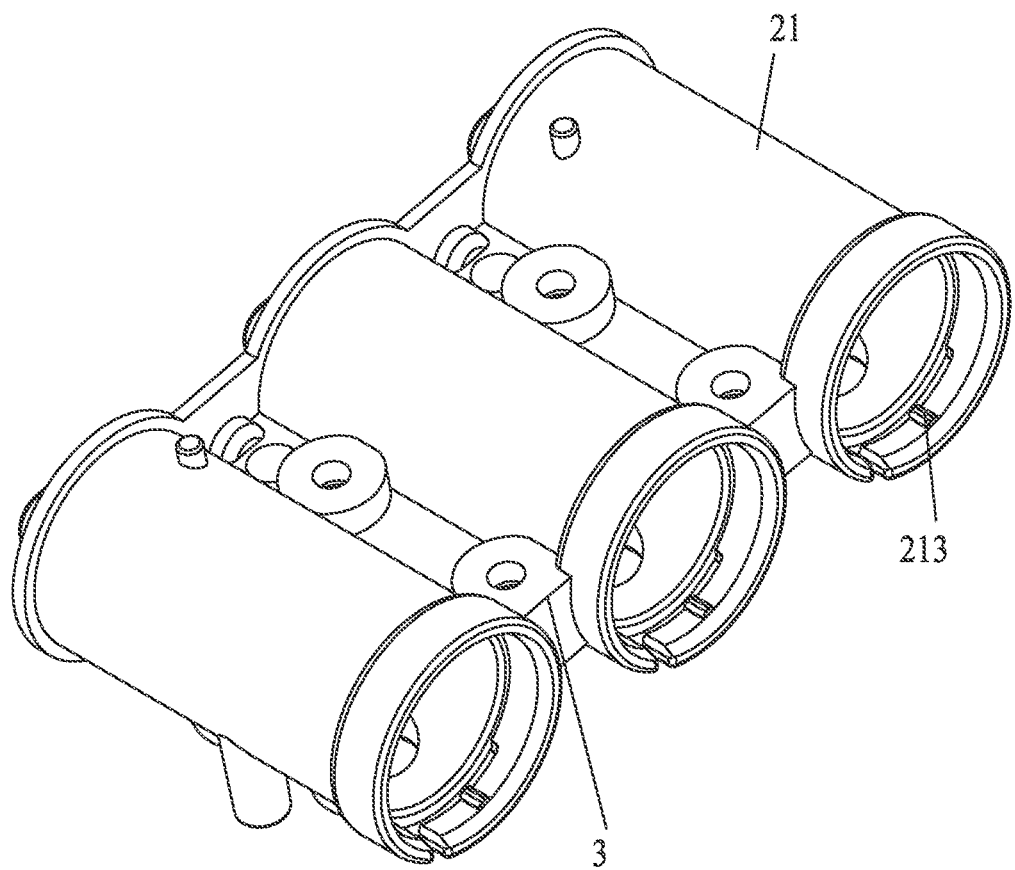
FIG. 5 is a schematic structural diagram of an outer sleeve in the present invention.
Figure 6:
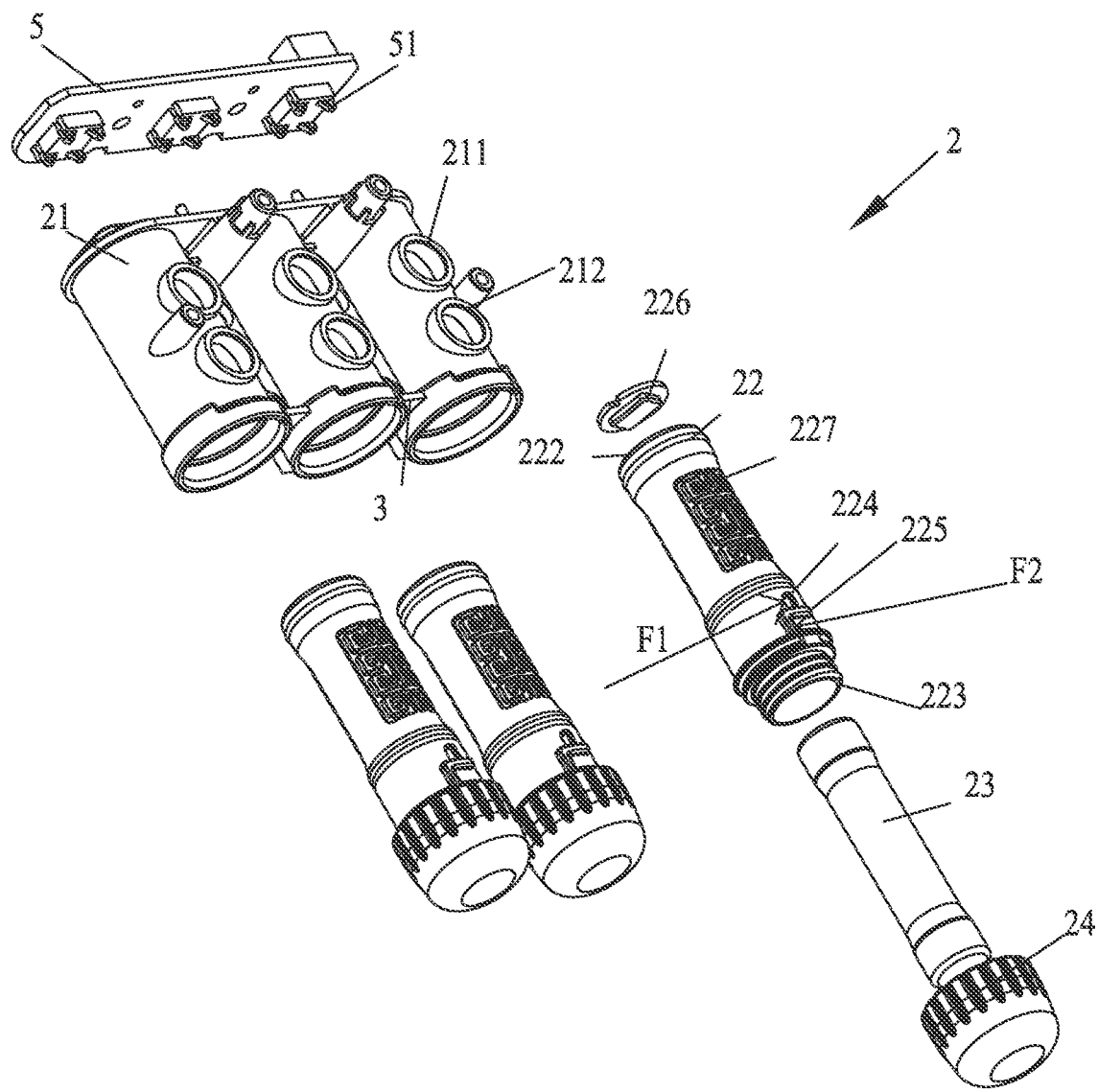
FIG. 6 is a schematic structural diagram of an essence box in the present invention.
Figure 7:
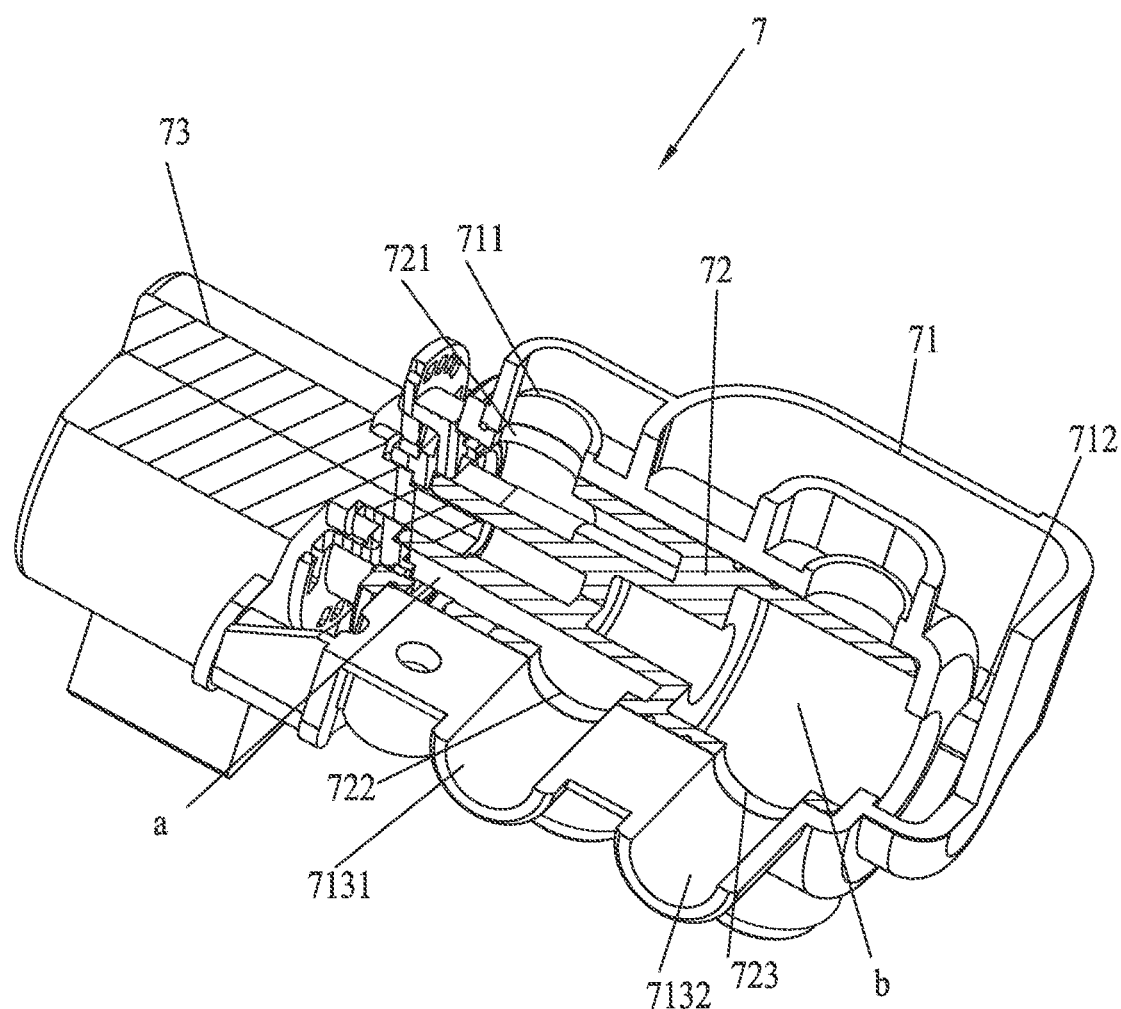
FIG. 7 is a schematic diagram of a fragrance switching assembly in an operating state I in the present invention.
Figure 8:
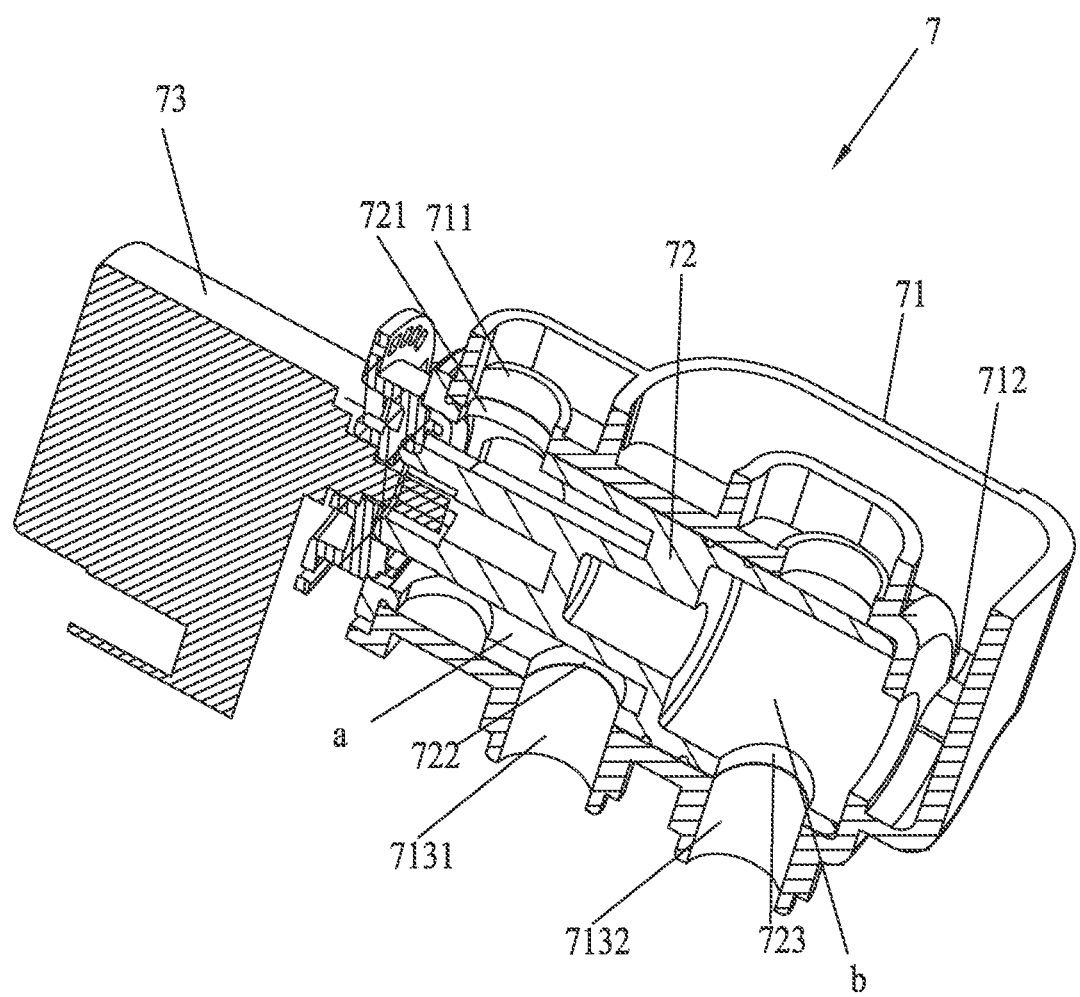
FIG. 8 is a schematic diagram of the fragrance switching assembly in an operating state II in the present invention.
Figure 9:
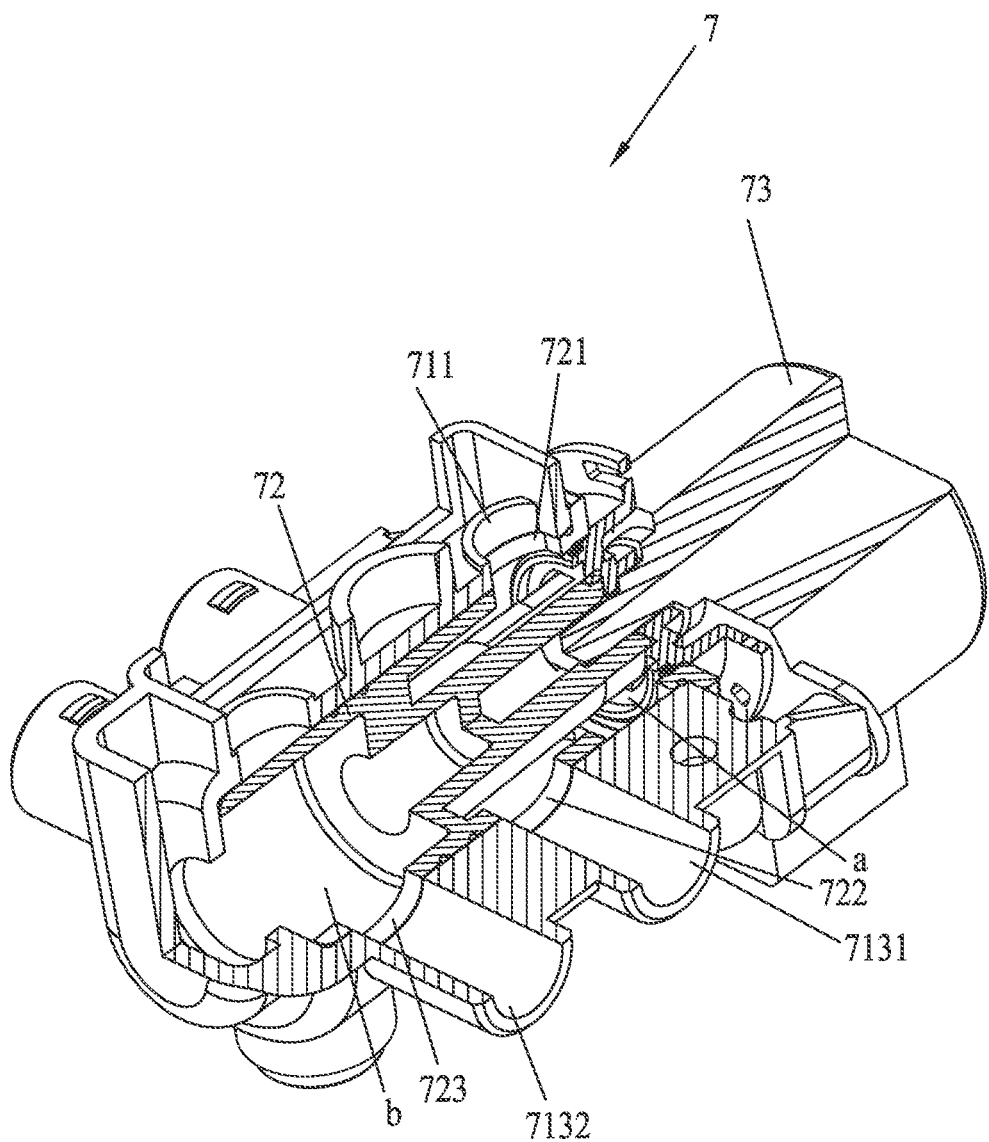
FIG. 9 is a schematic diagram of the fragrance switching assembly in an operating state III in the present invention.

Referring to FIGS. 3-4 and FIG. 6, the main control PCBA board 4 and the identification circuit board 5 are in communication connection. The identification circuit board 5 is provided with a plurality of pin connector groups 51. An ID identification chip 226 is embedded in a rear end portion of each of the inner sleeves 22, and each of the pin connector groups 51 is respectively connected to the corresponding one ID identification chip 226. The ID identification chip 226 is used to record the type of fragrance and other fragrance ID information of the essence box 2, so that the essence box 2 is identifiable. The identification circuit board 5 can read the ID identification chip 226, and send the read information such as the type of fragrance to the main control PCBA board 4. Then the information is sent by the main control PCBA board 4 to a terminal for display, such that the user can select the type of fragrance. The terminal may be a mobile terminal or a vehicle-mounted display screen.

In the present invention, the structure of the essence boxes 2 is brand-new. The essence boxes 2 can be directly placed inside the base 11 of the casing 1, the fragrance switching assembly 7 can be directly placed on the essence boxes 2, and the essence boxes 2 and the fragrance switching assembly 7 can be fixed without an additional fixing bracket, thereby saving the parts and simplifying the structure. Therefore, the volume of the fragrance generator 100 is effectively reduced, and the space taken up by the fragrance generator 100 is reduced.

In the description of the present invention, the terms "first" and "second" are only used for descriptive purposes, and cannot be construed as indicating or implying relative importance or implicitly indicating the number of the indicated technical features. Thus, the features defined with "first" and "second" may explicitly or implicitly include one or more of the features. In the description of the present invention, "a plurality of" means two or more than two, unless otherwise specifically defined.

Although the embodiments of the present invention have been shown and described above, it can be understood that the above embodiments are exemplary, and cannot be construed as limiting the present invention. Changes, modifications, replacements and variations of the above embodiments may be made by those of ordinary skill in the art within the scope of the present invention.

What is claimed is:

1. A vehicle-mounted intelligent fragrance generator, comprising a casing and a plurality of essence boxes; wherein the casing comprises a base; each of the plurality of essence boxes comprises an outer sleeve, an inner sleeve, an essence block and a fragrance front cover; the outer sleeve has a protrusion, and the protrusion is disposed at a front end portion of an inner wall of the outer sleeve; a rear end of the inner sleeve is a closed end, a front end of the inner sleeve is an open end, and the front end of an outer wall of the inner sleeve is provided with an anti-rotation strip; and the outer sleeve is fixed inside the base; the outer sleeve, the inner sleeve and the essence block are sequentially sleeved, the front end of the inner sleeve protrudes from the outer sleeve and extends out of the base, and the anti-rotation strip is clamped on the protrusion of the outer sleeve; and the fragrance front cover is located outside the base and fastened to a front end portion of the inner sleeve.

2. The vehicle-mounted intelligent fragrance generator according to claim 1, wherein a force applied on the anti-rotation strip by the protrusion of the outer sleeve is F1;

one side of the base is provided with a plurality of through holes, a convex ring is disposed in each of the plurality of through holes, and the convex ring is broken to form at least one notch and at least one arc strip;

the front end of the outer wall of the inner sleeve is further provided with at least one L-shaped protruding strip, and the at least one L-shaped protruding strip is located at a front of the anti-rotation strip; and the front end of the inner sleeve extends out of a through hole of the plurality of through holes of the base, a vertical edge of the at least one L-shaped protruding strip is located in the at least one notch, the at least one L-shaped protruding strip is stopped by the at least one arc strip, a circumferential force applied on the at least one L-shaped protruding strip by the arc strip is F2, and F2 and F1 are opposite in direction.

3. The vehicle-mounted intelligent fragrance generator according to claim 1, wherein outer sleeves are disposed in parallel and integrally formed, and a connecting rib is integrally formed between every two adjacent outer sleeves.

4. The vehicle-mounted intelligent fragrance generator according to claim 1, further comprising a draft fan and a fragrance switching assembly; wherein the casing further comprises a first air inlet and a first air outlet;

the outer sleeve further has an air inlet pipe port and an air outlet pipe port, and the outer wall of the inner sleeve has a plurality of fragrance diffusion holes; and the air inlet pipe port communicates with one fragrance diffusion hole of the plurality of fragrance diffusion holes, and the air outlet pipe port communicates with another fragrance diffusion hole of the plurality of fragrance diffusion holes; the air inlet pipe port and the air outlet pipe port of one of outer sleeves respectively communicate with an intake opening and a discharge opening of the draft fan through the fragrance switching assembly; and the intake opening of the draft fan communicates with the first air inlet, and the discharge opening of the draft fan communicates with the first air outlet.

5. The vehicle-mounted intelligent fragrance generator according to claim 4, wherein the casing further comprises an upper casing, and the upper casing is buckled on the base to form a containing cavity; the draft fan and the fragrance switching assembly are located in the containing cavity; and the draft fan, the fragrance switching assembly and the outer sleeve are sequentially disposed from top to bottom.

6. The vehicle-mounted intelligent fragrance generator according to claim 4, wherein the fragrance switching assembly comprises a shunt shaft sleeve, a shunt rotor and a motor; the shunt shaft sleeve is provided with a first air inlet pipe connector, a second air outlet and three sets of air pipes; the first air inlet pipe connector communicates with the first air inlet through the draft fan, and the second air outlet communicates with the first air outlet through the draft fan; each of the three sets of air pipes comprises an air inlet pipe and an air outlet pipe, wherein the air inlet pipe communicates with an air inlet pipe port of the outer sleeve, and the air outlet pipe communicates with an air outlet pipe port of the outer sleeve;

the shunt rotor comprises a plurality of third air inlets, a lead-in port and a lead-out port; the plurality of third air inlets are distributed along a circumferential direction of the shunt rotor; the lead-in port, the lead-out port and one of the plurality of third air inlets are distributed along an axial direction of the shunt rotor; the shunt rotor is rotatably disposed inside the shunt shaft sleeve;

the first air inlet pipe connector communicates with a third air inlet of the plurality of third air inlets and forms a clearance seal fit with the third air inlet; the air inlet pipe communicates with the lead-in port through a first channel inside the shunt rotor, and the lead-out port communicates with the second air outlet through a second channel inside the shunt rotor; and the motor drives the shunt rotor to rotate in the shunt shaft sleeve.

7. The vehicle-mounted intelligent fragrance generator according to claim 1, further comprising a main control printed circuit board assembly (PCBA) board and an identification circuit board for identifying a type of fragrance, wherein the main control PCBA board and the identification circuit board are in communication connection; the identification circuit board is provided with a plurality of pin connector groups; and an identity (ID) identification chip is embedded in a rear end portion of each of the inner sleeves, and each of the plurality of pin connector groups is respectively connected to the corresponding one ID identification chip.

8. The vehicle-mounted intelligent fragrance generator according to claim 1, further comprising a travel switch, wherein the travel switch comprises a motor, a control dial, a photoelectric switch and a main control PCBA board; and the motor drives a shunt rotor to rotate, the control dial is mounted on the shunt rotor, and the motor and the photoelectric switch are electrically connected to the main control PCBA board; and the control dial forms a clearance fit in the photoelectric switch, the control dial is provided with a plurality of sets of signal modules, each of the plurality of sets of signal modules comprises a locating module and a judgment module, the locating module is disposed next to the judgment module, and judgment modules in the plurality of sets of signal modules are different.

9. The vehicle-mounted intelligent fragrance generator according to claim 8, wherein the judgment module comprises at least one short hole, and a number of the at least short hole in each of the judgment modules is different; the locating module comprises a long hole; and a depth of the at least one short hole is less than a depth of the long hole.

* * * * *